US006984765B2

United States Patent
Reyes et al.

(10) Patent No.: US 6,984,765 B2
(45) Date of Patent: Jan. 10, 2006

(54) SEPARATION OF METHANOL, ETHANOL AND/OR DIMETHYL ETHER FROM HYDROCARBON MIXTURES

(75) Inventors: Sebastian C. Reyes, Branchburg, NJ (US); Venkatesan V. Krishnan, Mount Laurel, NJ (US); Gregory J. DeMartin, Flemington, NJ (US); John Henry Sinfelt, Oldwick, NJ (US); Karl G. Strohmaier, Port Murray, NJ (US); Jose Guadalupe Santiesteban, Baton Rouge, LA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 79 days.

(21) Appl. No.: 10/657,590

(22) Filed: Sep. 8, 2003

(65) Prior Publication Data

US 2005/0054885 A1    Mar. 10, 2005

(51) Int. Cl.
*C07C 1/20*    (2006.01)
*C07C 7/11*    (2006.01)

(52) U.S. Cl. ............... 585/639; 585/733; 585/809; 585/820; 585/826; 585/830; 568/699; 95/96; 95/115; 95/141; 95/900; 95/902

(58) Field of Classification Search ............ 568/699, 568/917, 922; 585/502, 533, 700, 733, 820, 585/852, 639, 809, 826, 830, 699; 95/96, 95/115, 141, 902
See application file for complete search history.

(56) References Cited

U.S. PATENT DOCUMENTS

| 4,310,440 | A | * | 1/1982 | Wilson et al. ............ 502/208 |
| 4,447,653 | A |   | 5/1984 | Vora ............................ 568/697 |
| 4,465,870 | A |   | 8/1984 | Herskovits .................. 568/697 |
| 4,605,787 | A |   | 8/1986 | Chu et al. ................... 568/697 |
| 4,734,199 | A |   | 3/1988 | Nagji et al. ................. 210/674 |
| 4,740,631 | A |   | 4/1988 | Nagji et al. ................. 568/697 |
| 4,748,281 | A |   | 5/1988 | Whisenhunt et al. ....... 568/697 |
| 4,814,517 | A |   | 3/1989 | Trubac ....................... 568/697 |
| 4,861,938 | A | * | 8/1989 | Lewis et al. ................ 585/640 |
| 5,026,482 | A |   | 6/1991 | Sircar ......................... 210/674 |
| 5,030,768 | A |   | 7/1991 | Chen et al. ................. 568/597 |
| 5,237,111 | A |   | 8/1993 | Yon et al. ................... 585/697 |
| 5,527,981 | A |   | 6/1996 | Valyocsik ................... 585/820 |
| 6,403,854 | B1 | * | 6/2002 | Miller et al. ................ 585/638 |
| 6,488,741 | B2 |  | 12/2002 | Olson ........................... 95/144 |
| 6,733,572 | B2 | * | 5/2004 | Reyes et al. .................. 95/96 |
| 2002/0144597 | A1 |  | 10/2002 | Olson ........................... 95/143 |
| 2003/0018228 | A1 |  | 1/2003 | Vaughn et al. .............. 585/500 |
| 2004/0254416 | A1 | * | 12/2004 | Risch et al. ................. 585/824 |

FOREIGN PATENT DOCUMENTS

| EP | 0 229 994 | 5/1989 |
| EP | 0 572 239 | 10/1996 |
| EP | 0 943 595 | 1/2002 |

OTHER PUBLICATIONS

M. Richter et al., "Molecular Sieving of n-Butenes by Microporous Silicoaluminophosphates", J. Chem. Soc. Chem. Commun. 21, 1616-1617 (1993).
Zhu et al., "Shape Selectivity in the Adsorption of Propane/Propene on the All-Silica DD3R", Chem. Commun. 2453-2454 (1999).
J. Crank, "The Mathematics of Diffusion", 2nd Ed., Oxford Univerisity Press, Great Britain, 203-253 (1975).
Reyes et al. in "Frequency Modulation Methods for Diffusion and Adsorption Measurements in Porous Solids", J. Phys. Chem. B. vol. 101, No. 4, pp. 614-622 (1997).

* cited by examiner

*Primary Examiner*—Rosalynd Keys

(57) ABSTRACT

The present invention is a separation process for producing a methanol, ethanol and/or dimethyl ether stream from a first stream containing $C_3+$ hydrocarbons. The first stream comprises $C_3+$ hydrocarbons, methanol, ethanol and/or dimethyl ether. The process comprises the step of passing the first stream through an adsorbent bed having a crystalline microporous material that preferentially adsorbs methanol, ethanol and/or dimethyl ether over the $C_3+$ hydrocarbons.

13 Claims, 5 Drawing Sheets

SEPARATION OF METHANOL, ETHANOL AND/OR DIMETHYL ETHER FROM HYDROCARBON MIXTURES

FIELD OF THE INVENTION

This invention relates to a process for separating methanol, ethanol and/or dimethyl ether from a hydrocarbon stream.

BACKGROUND OF THE INVENTION

The separation of low molecular weight species is an extremely important and large volume operation in the chemical and petrochemical industries—particularly in the production of ethylene and propylene. Steam cracking and catalytic cracking are among the largest industrial processes that produce ethylene and propylene. The oxygenate to olefins (OTO) process is another potential source of these streams. All of the above-mentioned processes require recovery and purification of ethylene and propylene to meet stringent product quality specifications. There are some byproducts that are more prevalent in an oxygenates to olefin plant than in a steam or catalytic cracking process. These include methanol, ethanol and dimethyl ether. The methanol, ethanol and dimethyl ether are often present in a stream with other low molecular weight hydrocarbons and oxygenates. The close proximity in boiling points between the various components in the effluent stream makes their separation by distillation expensive and difficult. Thus, there is a need to find alternative means for selectively recovering methanol, ethanol, and dimethyl ether from a C3+ hydrocarbon stream in a more energy-efficient and cost-effective manner. The majority of the C3+ hydrocarbons in the effluent stream of a methanol to olefins plant are propane, butanes and butenes.

Some of the leading alternative separation techniques to distillation involve the use of porous adsorbents that exploit their ability to selectively adsorb some of the components from a mixture. This has given rise to various forms of pressure or temperature swing adsorption (PSA/TSA) processes in which the mixture is first contacted with an adsorbent material under conditions where one or more of the components are selectively removed. The loaded material is then typically exposed to a lower pressure and/or higher temperature environment where the adsorbed components are released and recovered at a higher purity level. Economic viability requires adsorbent materials that can deliver high selectivity, high adsorption capacity, and short duration cycles. An additional and critically important requirement is that the adsorbent material should not catalyze or participate in chemical reactions that might lower the recovery of the desired components and/or render the adsorbent inactive.

There are at least four general categories of porous materials that have been proposed for applications in adsorption-based separation processes. They include ion exchange resins, mesoporous solids, activated carbons, and zeolites. Ion exchange resins and mesoporous solids usually exploit equilibrium adsorption properties in which one or more of the components are selectively adsorbed over suitably dispersed chemical agents. They principally rely on the adsorption affinity of cationic active centers such as Ag and Cu ions for the double bond in the olefins (e.g., $\pi$-complexation of propylene). Since these materials rely on adsorption equilibrium properties to effect the separation, the diffusion rates of the various components within the adsorbent do not influence the selectivity of the separation process. Rapid diffusion of the species in and out of the adsorbent material is, however, desirable in order to speed up the contacting of the species with the adsorption sites, leading to adsorption/desorption cycles that have a short duration. Since the pore sizes in these materials are relatively large compared to molecular dimensions, diffusion is generally fast. Thus, the characteristic time associated with the adsorption/desorption cycle is largely controlled by the time required to bring the mixture into thermodynamic equilibrium with the adsorbent. On the other hand, in addition to the basic requirement of adsorption affinity, activated carbons and zeolites can further improve the effectiveness of the separation process by controlling the rates at which molecules diffuse in and out of the material. The diffusional effects in these cases, which are exploited advantageously, are a consequence of the small pore sizes, of molecular dimensions, that make up these high surface area carbons and zeolites. Two limiting cases of diffusion control are frequently exploited for applications in separation. In one extreme case, the separation is achieved by preventing the diffusion of some of the components into the adsorbent. This is generally referred to as separation by size exclusion and can lead to high separation selectivity. The second case exploits a sufficiently large difference in diffusion rates that allows the preferential uptake of some of the components within a predetermined adsorption time. This case is generally known as a kinetic-based separation scheme because the degree of separation depends on the duration of this predetermined adsorption time. Thus, carbons are usually activated to very high surface areas in order to provide textural properties and pore sizes that maximize the number of adsorption sites per unit mass of the material while selectively controlling diffusional transport in and out of the structure. In many applications, zeolites have become even more attractive than activated carbons because of the ever-increasing possibilities afforded by new synthetic routes, which allow for a more flexible and precise control of chemical composition and structure. Whereas chemical composition is used primarily for controlling adsorption affinity, structural properties are used for controlling diffusion rates. The tetrahedrally coordinated atoms in these microporous crystalline materials form ring structures of precise dimensions that selectively control the diffusional access to the internal pore volume.

Eight-membered ring zeolites, in particular, have been actively investigated for the separation of low molecular weight hydrocarbons because their window sizes are comparable to molecular dimensions and because they can provide high adsorption capacities. A typical example is the Linde type A zeolite, which is characterized by a set of three-dimensional interconnected channels having 8-membered ring window apertures. The effective size of the windows can be controlled by appropriately selecting the type of charge-balancing cations. This has given rise to the potassium (3A), sodium (4A) and calcium (5A) forms, which have nominal window sizes of about 3 Å, 3.8 Å, and 4.3 Å, respectively.

In applications involving zeolites, it is well known that the control of window size is critically important for achieving high separation selectivity. For a given zeolite structure type, the effective size of the windows can, in some cases, be modified by partially blocking or unblocking the windows with pre-selected charge-balancing cations. Care must be taken that the adsorbent material does not have any residual acidity and/or that the charge-balancing cations do not promote or participate in detrimental reactions. These reactions not only lower the recovery of the desired components, but they are also likely to render the adsorbent inactive. The double bonds in the olefins are particularly prone to attack even by mildly acidic sites (e.g., isomerization, oligomerization, polymerization, etc) and this may severely limit the temperature and partial pressures at which the separation process can be carried out. The problems of residual acidity are illustrated, for example, by the work M. Richter et al., "Sieving of n-Butenes by Microporous Silicoaluminophosphates", J. Chem. Soc. Chem. Commun. 21, 1616–1617 (1993), where a proposal is made for the use of SAPO-17 (ERI) for separating trans-2-butene from 1-butene and cis-2-butene. Their work indicates detrimental catalytic activity with their material even at mild temperatures (395K).

Patent EP-B-572239 discloses a PSA process for separating an alkene, such as propylene, from a mixture comprising said alkene and one or more alkanes by passing the mixture through at least one bed of zeolite 4A at a temperature above 273K to preferentially adsorb said alkene and then desorbing the alkene from the bed. EP-A-943595 describes a similar process in which the zeolite adsorbent is zeolite A having, as its exchangeable cations, about 50% to about 85% of sodium ions, about 15% to about 40% of potassium ions and 0% to about 10% of other ions selected from Group IA ions (other than sodium and potassium), Group IB ions, Group IIA ions, Group IIIA ions, Group IIIB ions and lanthanide ions. These patents illustrate the use of suitably chosen charge-balancing cations for controlling chemical composition and the window sizes of the adsorbents.

Zhu et al., "Shape Selectivity in the Adsorption of Propane/Propene on the All-Silica DD3R", Chem. Commun. 2453–2454 (1999), reports an example that fits the category of separation by size exclusion. Their adsorption uptake measurements indicate that only propylene is able to access the interior of the DD3R crystallites. The exclusion of propane from the adsorbent interior was suggested as the basis for a very selective adsorption scheme.

U.S. Pat. No. 4,605,787 discloses the use of an adsorption-based process for recovering unreacted methanol that is found as an admixture with methyl tert-butyl ether (MTBE) product resulting from the reaction of a C4 stream (e.g., isobutylene) with an excess of methanol. It proposes the use of small pore, 8-membered rings, zeolites 3A, 4A, 5A, and chabazite to selectively adsorb the unreacted methanol from the MTBE product and then desorbing and recycling the methanol by passing the C4 feed stream of the MTBE process as a purge at elevated temperature. The claimed selective adsorption of the methanol by the proposed adsorbents and the recovery of the substantially methanol-free MTBE product suggests that the mechanism of separation is by size exclusion. Such mechanism is also consistent with the sizes of the methanol and MTBE molecules in relationship with the pore sizes of the proposed adsorbents.

U.S. Pat. No. 6,488,741 discloses the use of small pore, 8-membered ring, materials for the kinetic-based separation of propylene from propane. Sorption uptake measurements of propylene and propane on pure silica materials such as CHA, ITE, and ZSM-58 indicate that propylene diffuses much more rapidly than propane and this large difference in diffusion rates is used as a basis for a kinetic-based separation scheme in which propylene and propane mixtures can be separated into their individual components with a high degree of selectivity.

The rate of diffusion of a gaseous species in a porous crystalline material is conveniently characterized in terms of its diffusion time constant, $D/r^2$ (s-1), wherein D is the Fickian diffusion coefficient (cm2/sec) and r is the radius of the crystallites (cm) characterizing the diffusion distance. In situations where the crystals are not of uniform size and geometry, r represents a mean radius representative of their corresponding distributions. The required diffusion time constants can be derived from standard sorption uptake kinetics measurements as described, for example, by J. Crank in "The Mathematics of Diffusion", 2nd Ed., Oxford University Press, Great Britain, 1975 or by frequency response methods as described, for example, by Reyes et al. in "Frequency Modulation Methods for Diffusion and Adsorption Measurements in Porous Solids", J. Phys. Chem. B. 101, pages 614–622, 1997.

As noted, there is a need for new, more energy-efficient, adsorption-based methods for selectively recovering methanol, ethanol and/or dimethyl ether from a C3+ hydrocarbon stream. Suitable adsorbents for this application are those having no residual acidity, having high adsorption capacities, and which can be operated in adsorption/desorption cycles of short duration. Short cycles are important for achieving high throughputs that are economically viable. These requirements are well satisfied by the materials and processes of the present invention described below.

SUMMARY OF THE INVENTION

The present invention is a process for recovering methanol, ethanol and/or dimethyl ether (typically methanol) from a C3+ hydrocarbon stream. The process comprises the step of passing the C3+ hydrocarbon stream comprising C3+ hydrocarbons, methanol, ethanol and/or dimethyl ether through an adsorbent bed. The adsorbent bed comprises a non-acidic, 8-membered ring crystalline microporous material with no extra-framework charge balancing cations. The crystalline microporous material preferentially adsorbs methanol, ethanol and/or dimethyl ether over C3+ hydrocarbons to reduce the concentration of methanol, ethanol and/or dimethyl ether in the C3+ hydrocarbon stream.

According to one embodiment, there is a further step of desorbing the methanol, ethanol and/or dimethyl ether from the adsorbent bed.

In yet another embodiment, there is a process for making a propylene stream and a propane stream from an oxygenate feed stream. The process comprises the steps of contacting an oxygenate feed stream with a molecular sieve catalyst under conditions sufficient to make a first stream. The first stream comprises propylene, propane and dimethyl ether. At least a majority of the propylene in the first stream is separated from propane in the first stream to form a propylene product stream. Furthermore, dimethyl ether is adsorbed from propane with a crystalline microporous material that preferentially adsorbs dimethyl ether over propane to form a propane stream. Then, dimethyl ether is desorbed from the adsorbent bed including the microporous material.

In still another embodiment, there is a separation process for producing a dimethyl ether and/or methanol stream from a first stream. The first stream comprises propane, dimethyl ether and/or methanol. The process comprises the step of passing the first stream through an adsorbent bed having a non-acidic, 8-membered ring crystalline microporous material with no extra-framework charge balancing cations that preferentially adsorbs dimethyl ether and/or methanol over propane. Furthermore, dimethyl ether and/or methanol are desorbed from the crystalline microporous material.

In one embodiment, there is a process for recovering methanol, ethanol and/or dimethyl ether from a C3+ hydrocarbon stream. This process comprises the step of passing the C3+ hydrocarbon stream comprising C3+ hydrocarbons, methanol, ethanol and/or dimethyl ether through an adsorbent bed. The adsorbent bed comprises a crystalline microporous material having a chabazite-type framework and having a composition involving the molar relationship defined as follows:

$$X_2O_3:(n)YO_2,$$

wherein X is a trivalent element, Y is a tetravalent element and n is greater than 100, preferably greater than 200, more preferably greater than 500, most preferably greater than 1000. Optionally, X is selected from the group consisting of aluminum, boron, iron, indium, and/or gallium, and more preferably includes aluminum. Optionally, Y is selected from a group consisting of silicon, tin, titanium and/or germanium, and preferably includes silicon.

In still another embodiment, the step of passing or alternatively the steps of adsorbing and/or desorbing occurs in a kinetic-based pressure and/or temperature swing adsorption process.

The crystalline microporous material, of one embodiment, adsorbs methanol, ethanol and/or dimethyl ether (typically methanol) within an adsorption time of about 120 seconds or less, preferably of about 90 seconds or less; or more preferably of about 60 seconds or less.

According to an embodiment, the step of passing or alternatively the step of adsorbing occurs within a temperature ranging from about 273K to about 523K and typically occurs within a pressure ranging from about 100 kPa to about 2000 kPa.

In one embodiment, the C3+ hydrocarbon stream, the first stream or optionally the propane stream is in a vapor phase during the step of passing or absorbing.

In one embodiment, the C3+ hydrocarbon stream comprises C4+ hydrocarbons. In another embodiment, the C3+ hydrocarbon stream comprises ether.

In still another embodiment, the crystalline microporous material has a system of three interconnecting 8-membered ring channels.

Optionally or alternatively, the crystalline microporous material contains framework silicon. Particularly, the crystalline microporous material is Si-CHA, DDR, or ITE.

In one embodiment the crystalline microporous material contains framework phosphorus. Particularly, the crystalline microporous materials are from a group consisting of AlPO-34, AlPO-18, GaPO-34 and GaPO-18. In another embodiment, the crystalline microporous material is AlPO-34, AlPO-18, GaPO-34, or GaPO-18.

In another embodiment, there is a process for producing polypropylene comprising producing a propylene stream from or by any of the foregoing processes and polymerizing the propylene stream to produce polypropylene.

DETAILED DESCRIPTION OF THE INVENTION

Figure 1:
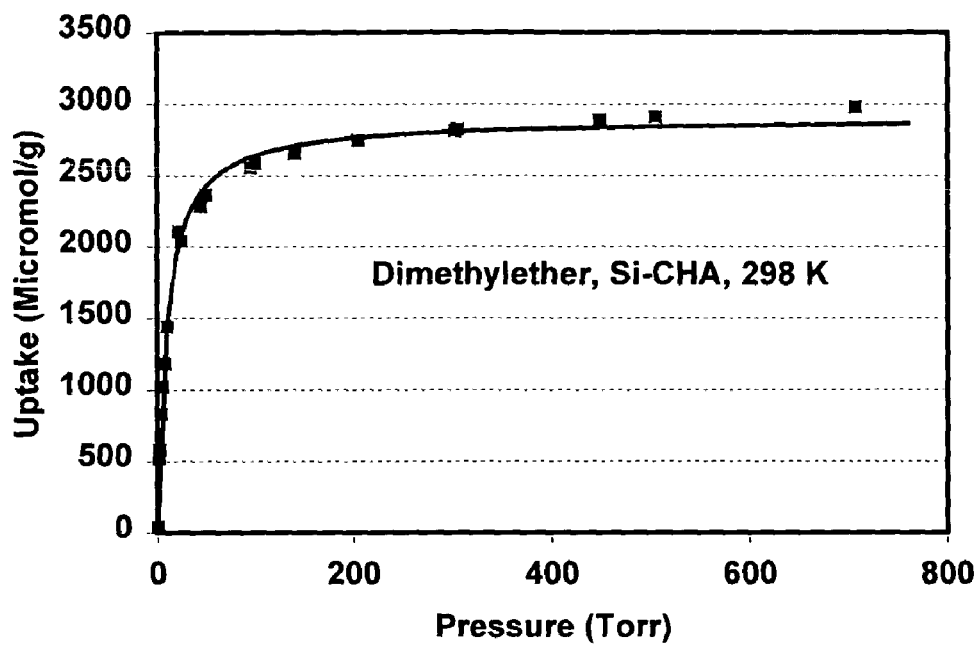
FIG. 1 is a plot showing the adsorption uptake of dimethyl ether on silica chabazite (Si-CHA) at 298K.

The present invention is a process for recovering methanol, ethanol and/or dimethyl ether from a C3+ hydrocarbon stream. The process of one embodiment comprises the step of contacting the C3+ hydrocarbon stream comprising C3+ hydrocarbons, methanol, ethanol and/or dimethyl ether with an adsorbent bed during a predetermined period of time. The adsorbent bed comprises a non-acidic, 8-membered ring crystalline microporous material. The crystalline microporous material preferentially adsorbs methanol, ethanol and dimethyl ether over the C3+ hydrocarbons to form a C3+ hydrocarbon stream haveing a substantially reduced concentration of methanol, ethanol and/or dimethyl ether.

In one embodiment, the porous crystalline material used in the process of the invention contains framework phosphorus and has at least one system of channels, each defined by an 8-membered ring of tetrahedrally coordinated atoms. Typically, the porous crystalline material is non-acidic. Suitable porous crystalline materials for use as the adsorbent in the process of the invention include silicates, aluminosilicates, aluminophosphates, gallophosphates, galloaluminophosphates, metalloaluminophosphates and metalluminosilicophosphates. Particularly preferred materials include silica chabazite (Si-CHA) the aluminophosphates AlPO-34 and AlPO-18 and their corresponding gallophosphates GaPO-34 and GaPO-18. AlPO-34 and its synthesis are described in F. Guth, PhD Thesis, Mulhouse Univ., France (1989) or in H. Halvorsen, PhD Thesis, Univ. of Oslo, Norway (1996), whereas AlPO-18 and its synthesis are described in U.S. Pat. Nos. 4,310,440 and 4,385,994, the entire contents of which are incorporated herein by reference.

Optionally or alternatively, the crystalline microporous material is a silicate material. Particularly, the crystalline microporous material is Si-CHA (silica chabazite), DDR (deca dodecasil 3R), or ITE (ITQ-3). Si-chabazite is described in Diaz-Cabanas, et al., Synthesis and structure of pure SiO2 chabazite: the SiO2 polymorph with the lowest framework density, Chem. Commun., pp. 1881–82 (1998), including the method of making silica chabazite. Deca dodecasil 3R is described in Gies, H. Z., Studies on clathrasils. IX. Crystal structure of deca-dodecasil 3R, the missing link between zeolites and clathrasils, Kristallogr., Vol. 175, pp. 93–104 (1986); Stewart, A et al. Synthesis and characterisation of crystalline aluminosilicate Sigma-1, Stud. Surf. Sci. Catal., Vol. 37, pp. 57–64 (1988) and U.S. Pat. No. 4,698,217. ITE (ITQ-3) is described in Camblor, M. A. et al, Synthesis and structure of ITQ-3, the first pure silica polymorph with a two-dimensional system of straight eight-ring channels, Angew. Chem., Int. Ed., Vol. 36, 2659–2661 (1997).

In another embodiment of the present invention, the porous crystalline material is a high silica chabazite containing the necessary charged-balancing cations such that any residual acidity is removed. The chabazite of the present invention has a composition involving the molar relationship defined as follows:

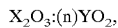

wherein X is a trivalent element, such as aluminum, boron, iron, indium, and/or gallium, typically aluminum; Y is a tetravalent element, such as silicon, tin, titanium and/or germanium, typically silicon; and n is greater than 100 and typically greater than 200, preferably greater than about 500, more preferably greater than 1000.

In its as-synthesized form, the chabazite of the present invention has a composition involving the molar relationship defined as follows:

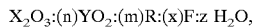

wherein X, Y and n are as defined in the preceding paragraph and wherein m ranges from about 15 to about 350, such as from about 30 to about 50, z ranges from about 0 to about 10, and x ranges from about 7 to about 175, such as from about 15 to about 25.

The chabazite of the invention can be prepared from a reaction mixture containing sources of water, an oxide of a trivalent element X, an oxide of a tetravalent element Y, an organic directing agent (R) as described below, and fluoride ions, said reaction mixture having a composition, in terms of mole ratios of oxides, within the following ranges:

| Reactants | Useful | Typical |
|---|---|---|
| H$_2$O/YO$_2$ | 2–40 | 2–5 |
| F/YO$_2$ | 0.2–1.0 | 0.3–0.7 |
| R/YO$_2$ | 0.2–2.0 | 0.3–1.0 |
| X$_2$O$_3$/YO$_2$ | 0.00025–0.02 | 0.0005–0.01 |

The organic directing agent R used herein is conveniently selected from N-alkyl-3-quinuclidinol, N,N,N-tri-alkyl-1-adamantammonium cations, N,N,N-trialkyl-exoaminonorbornane and mixtures thereof and typically is a N,N,N-trimethyl-1-adamantammonium cation.

Crystallization can be carried out at either static or stirred conditions in a suitable reactor vessel, such as for example, polypropylene jars or Teflon™-lined or stainless steel autoclaves, at a temperature of about 373K to about 498K for a time sufficient for crystallization to occur at the temperature used, e.g., from about 16 hours to about 7 days. Synthesis of the new crystals may be facilitated by the presence of at least 0.01 percent, such as at least 0.10 percent, for example at least 1 percent, seed crystals (based on total weight) of the crystalline product. After crystallization is complete, the crystals are separated from the mother liquor, washed and calcined to remove the organic directing agent. Calcination is typically conducted at a temperature of about 643K to about 1198K for at least 1 minute and generally not longer than 20 hours.

As shown in the examples, equilibrium adsorption isotherms and dynamic diffusion studies confirm that Si-CHA has high potential for selectively recovering dimethyl ether and methanol from mixtures of C3+ hydrocarbons. Si-CHA is non-reactive, exhibits a high adsorption capacity and rapidly adsorbs dimethyl ether and methanol while relatively hindering the diffusion of C3+ hydrocarbons.

High silica chabazite is likewise effective for selectively recovering methanol, ethanol and/or dimethyl ether from C3+ hydrocarbons. The inherent and low acidity of high silica chabazite can be completely removed by the addition of suitable charge-balancing cations.

AlPO-18 and AlPO-34 are capable of separating methanol, ethanol and/or dimethyl ether from C3+ hydrocarbons and particularly propylene and butylene. They are non-reactive, exhibit a high adsorption capacity and rapidly adsorb methanol, ethanol and/or dimethyl ether while relatively hindering the diffusion of C3+ hydrocarbons. However, while AlPO-34 and AlPO-18 appear to be excellent materials for separating methanol, ethanol and/or dimethyl ether from C3+ hydrocarbons and particularly propylene and butylene, there are many other phosphorus-containing crystalline microporous materials that could deliver equal or even improved performance depending on the optimum conditions. Likewise, there are many other non-acidic, eight-member crystalline microporous materials with no charge balancing cations that could deliver equal or even improved performance depending on the optimum conditions for the separation.

Thus, for example, one can envision process conditions in which shorter cycle times are obtained at the expense of decreased separation selectivity (i.e., lower purity). A material with slightly greater window size could optimize performance under these conditions. Alternatively, if improvements in separation selectivity justify slightly longer cycle times, it is advantageous to incorporate selected metals into the framework in such a manner that the effective size of the windows is slightly reduced. In general, the materials needed for specific situations can be optimized by suitable choices of the type of microporous structure, the framework atoms, and the type and charge of any non-framework balancing cations provided that any detrimental chemistry is avoided.

The process of the invention can be carried out in a system comprising a single adsorption bed or a plurality of adsorption beds operated either in phase or out of phase. With a system comprising a single adsorption bed or a plurality of beds operated in phase, the adsorption step must be periodically stopped to permit regeneration of the adsorbent bed(s), whereas when a plurality of adsorption beds are employed in parallel and operated out of phase, one or more beds can be in adsorption service adsorbing the desired gas component, while one or more other units are undergoing regeneration to desorb and collect the adsorbed gas component. Operation of the adsorption process of the invention is cyclical. In the preferred adsorption process, cycles are repeatedly carried out in a manner such that production of the desired product gas is substantially continuous. In the preferred embodiment, therefore, the process is carried out in a system comprising a plurality of adsorption beds arranged in parallel and operated out of phase, such that at least one bed is always in the adsorption phase while another is always in the adsorbent regeneration phase.

The process of the invention may be operated as either a pressure swing adsorption (PSA) process or a temperature swing adsorption (TSA) process. In either case, the precise steps used in carrying out the separation are not critical to the invention.

In general, the basic steps in a PSA process include an adsorption vessel pressurization step, a production (adsorption) step and an adsorbent regeneration step. During the vessel pressurization step, the pressure in the adsorption vessel in which the adsorption process is carried out is raised to the desired adsorption pressure. During the production step, a first stream comprising C3+ hydrocarbons, methanol, ethanol and/or dimethyl ether is passed through the adsorption vessel at the desired adsorption pressure. As the first stream passes through the adsorption vessel, a methanol, ethanol and/or dimethyl ether-enriched component is adsorbed and a methanol, ethanol and/or dimethyl ether-depleted non-adsorbed gas fraction passes out of the adsorption vessel. The bed regeneration step is carried out by reducing the pressure in the adsorption vessel so as to recover the desired methanol, ethanol and/or dimethyl ether-enriched product gas from the vessel.

The temperature at which the adsorption step of the PSA process, in one embodiment, is generally between about 273K and about 523K, or more preferably between about 323K and about 523K. The upper temperature is selected so as to achieve a significant loading onto the adsorbent material (i.e., weight percent gain) and to avoid the possibility of any unwanted reactions, such as oligomerization and/or polymerization of the olefins in the stream. The pressures at which the adsorption and adsorbent regeneration steps are carried out are likewise a matter of choice and, in general, these steps can be carried out at any of the usual pressures that are typically employed for gas PSA processes. The pressure at which the adsorption step is carried out is determined by economics. Typically, the adsorption step is carried out at methanol and /or ethanol and/or dimethyl ether partial pressures in the range of about 3 kPa to about 300 kPa, and preferably in the range of about 5 kPa to about 200 kPa. Typically, the adsorbent regeneration step is carried out at methanol and /or ethanol and/or dimethyl ether partial pressures in the range of about 0.1 kPa to about 10 kPa, and preferably in the range of about 0.2 kPa to about 5 kPa.

The crystalline microporous material, of one embodiment, adsorbs methanol, ethanol and/or dimethyl ether within an adsorption time of about 120 seconds or less, preferably of about 90 seconds or less; or more preferably of about 60 seconds or less.

In one embodiment, the C3+ hydrocarbon stream, the first stream or optionally the propane stream is in a vapor phase during the step of passing or adsorbing. In another embodiment, the C3+ hydrocarbon stream comprises C4+ hydrocarbons. In still another embodiment, the C3+ hydrocarbon stream comprises dimethyl ether.

Where the process of invention is operated as a TSA process, the production (adsorption) step is carried out at a first temperature and an adsorbent regeneration step is carried out at a second higher temperature so as to desorb the methanol and/or ethanol and/or dimethyl ether-enriched component adsorbed during the production step. In this case, the adsorption step is carried out at temperatures in the range of about 273K to about 473K, preferably in the range of about 323K to about 423K, while the adsorbent regeneration step is carried out at temperatures in the range of about 373K to about 573K, preferably in the range of about 423K to about 523K. The adsorption and regeneration steps in a TSA process are typically carried out at methanol and/or ethanol and/or dimethyl ether partial pressures in the range of about 10 kPa to about 300 kPa, and preferably in the range of about 20 kPa to about 200 kPa.

The present invention is useful in the recovery section of an oxygenate to olefin reaction. In an oxygenate to olefin reaction, an oxygenate feed stream is fed into an oxygenate-to-olefin reactor producing a reactor effluent stream. The reactor uses a catalyst, for example, a molecular sieve catalyst that comprises a molecular sieve catalyst composition.

As noted, oxygenate-to-olefin processes typically use molecular sieve catalysts or molecular sieve catalyst compositions. The molecular sieve catalyst compositions have molecular sieve and binder and/or matrix material. The molecular sieve catalysts are prepared according to techniques that are known to a person of ordinary skill in the art. Molecular sieves and their method of manufacture are disclosed in PCT Publication Nos. WO 03/000412 and WO 03/000413, the contents of which are incorporated herein by reference.

Preferably, the molecular sieve is a zeolitic or zeolitic-type molecular sieve. Alternatively, the preferred molecular sieve is an aluminophosphate (AlPO) molecular sieves and/or silicoaluminophosphate (SAPO) molecular sieves and substituted, preferably metal substituted, AlPO and/or SAPO molecular sieves including the molecular sieves that are intergrowth materials having two or more distinct phases of crystalline structures within one molecular sieve composition.

Binder materials that are useful alone or in combination include various types of hydrated alumina, silicas, and/or other inorganic oxide sol. In one embodiment, the binders are alumina sols including Nalco 8676 available from Nalco Chemical Co., Naperville, Ill. and Nyacol available from The PQ Corporation, Valley Forge, Pa. Preferably in one embodiment, the binder does not have acid activity.

Matrix materials include one or more of: rare earth metals, metal oxides including titania, zirconia, magnesia, thoria, beryllia, quartz, silica or sols, and mixtures thereof, for example, silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Georgia and Florida clays. Non-limiting examples of other matrix materials include: haloysite, kaolinite, dickite, nacrite, or anauxite. Preferably, in one embodiment, the matrix material used does not have acid activity.

Molecular sieve catalysts are useful for conversion of a feed stream that contains one or more aliphatic-containing compounds. The one or more aliphatic-containing compounds are disclosed in PCT Publication Nos. WO 03/000412 and WO 03/000413, the contents of which are incorporated herein by reference.

In a preferred embodiment of the process of the invention, the aliphatic feed stream is an oxygenate feed stream. Particularly, an oxygenate feed stream is a feed stream that comprises one or more organic compound(s) containing at least one oxygen atom. Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the oxygenate feed stream comprises oxygenates selected from one or more of methanol, ethanol, dimethyl ether, diethyl ether or a combination thereof, more preferably methanol and dimethyl ether, and most preferably methanol.

In one embodiment, the oxygenate feed stream is produced from an integrated process for producing oxygenates, particularly alcohols, from a hydrocarbon feedstock, preferably a hydrocarbon gas feedstock, more preferably methane and/or ethane. A method of preparing an alcohol feedstock is disclosed in PCT Publication Nos. WO 03/000412 and WO 03/000413, the contents of which are incorporated herein by reference. The methanol production process produces an oxygenate containing stream, or crude methanol, typically contains the alcohol product (including methanol, ethanol and fusel oil) and various other components such as ethers, particularly dimethyl ether, ketones, aldehydes, as well as dissolved gases such as hydrogen methane, carbon dioxide and nitrogen. The oxygenate containing stream, crude methanol, in the preferred embodiment is passed through a well known purification processes, distillation, separation and fractionation, resulting in a purified oxygenate containing stream, for example, commercial Grade A and AA methanol. This purified oxygenate containing stream is used in one embodiment as the oxygenate feed stream. Non-limiting examples of a process for producing an oxygenate feed stream from hydrocarbons and using it to produce olefin(s) is described in EP-B-0 933 345, which is herein fully incorporated by reference.

The aliphatic feed stream, preferably oxygenate feed stream, discussed above is converted primarily into one or more olefin(s). The olefin(s) or olefin monomer(s) produced from the aliphatic feed stream typically have from 2 to 30 carbon atoms, preferably 2 to 8 carbon atoms, more preferably 2 to 6 carbon atoms, still more preferably 2 to 4 carbons atoms, and most preferably ethylene and/or propylene.

Non-limiting examples of olefin monomer(s) include ethylene, propylene, butylene-1, pentene-1, 4-methyl-pentene-1, hexene-1, octene-1 and decene-1, preferably ethylene, propylene, butylene-1, pentene-1, 4-methyl-pentene-1, hexene-1, octene-1 and isomers thereof. Other olefin monomer(s) include unsaturated monomers, diolefin(s) having 4 to 18 carbon atoms, conjugated or non-conjugated dienes, polyenes, vinyl monomers and cyclic olefin(s). PCT Publication Nos. WO 03/000412 and WO 03/000413 for a more complete description of the olefin(s) produced, the content of these publications are incorporated herein by reference. Most preferably, the olefin(s) produced are ethylene, propylene or butylene often referred to as prime olefin(s) or light olefin(s).

The aliphatic feed stream, preferably an oxygenate feed stream, in one embodiment, contains one or more diluents, typically used to reduce the concentration of the active ingredients in the oxygenate feed stream, and are generally non-reactive to the active ingredients in the oxygenate feed stream or molecular sieve catalyst composition. Non-limiting examples of diluents are disclosed in PCT Publication Nos. WO 03/000412 and WO 03/000413, the contents of which are incorporated herein by reference. The most preferred diluents are water and nitrogen, with water being particularly preferred.

The process for converting an aliphatic feed stream, especially an oxygenate feed stream in the presence of a molecular sieve catalyst composition is carried out in a reaction process in a reactor, where the process is a fixed bed process, a fluidized bed process, preferably a continuous fluidized bed process, and most preferably a continuous high velocity fluidized bed process.

The reaction processes can take place in a variety of catalytic reactors such as hybrid reactors that have a dense bed or fixed bed zones and/or fast fluidized bed reaction zones coupled together, circulating fluidized bed reactors, riser reactors, and the like. Suitable conventional reactor types are described in, for example, U.S. Pat. No. 4,076,796, U.S. Pat. No. 6,287,522 (dual riser), and Fluidization Engineering, D. Kunii and O. Levenspiel, Robert E. Krieger Publishing Company, New York, N.Y. 1977, which are all herein fully incorporated by reference.

The preferred oxygenate-to-olefin reactor is a riser reactor. Riser reactors are generally described in Riser Reactor, Fluidization and Fluid-Particle Systems, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In one embodiment, the reactor effluent stream comprises ethylene and propylene, C4+ olefin(s), methane, C2+ paraffins, water, unreacted oxygenate(s), and oxygenated hydrocarbons. In another embodiment, the reactor effluent stream comprises from about 30 wt. % to about 70 wt. % water, preferably, from about 35 wt. % to about 70 wt. % water; more preferably from about 40 wt. % to about 65 wt. % water expressed as a percentage of the total weight of the reactor effluent stream.

In the embodiment, the reactor effluent stream exits the reactor through particle size separators to separate the catalyst from the reactor effluent stream. In this embodiment, the reactor effluent stream typically contains catalyst fines, i.e. Catalyst particles that have a diameter less than that retained by the particle size separators. According to one embodiment, the reactor effluent stream has about 2 wt. % or less, preferably about 1 wt. % or less, more preferably from about 0.005 wt. % to about 0.5 wt. % catalyst fines based upon the total weight of the reactor effluent stream.

In one embodiment, the reactor effluent stream passes through a heat exchanger system to cool the reactor effluent stream. According to one embodiment, the heat exchanger system comprises one or more heat exchanger services, preferably two to four heat exchanger services, most preferably two or three heat exchanger services.

Following optional cooling, the effluent stream, of one embodiment, travels to a quench device. The reactor effluent stream is quenched with a quench medium in the quench device. As used herein, a "quench device" is a device for removing a portion of the effluent stream (including the reactor effluent stream or the cooled effluent stream) by establishing a sufficient quantity of liquid quench medium in contact with a gaseous reactor effluent stream which condenses at least a portion of the material in the reactor effluent stream. One example of a quench device in an oxygenate-to-olefin product stream is found in U.S. Pat. No. 6,121,504 (direct product quench) fully incorporated herein by reference.

As previously described, the effluent stream is quenched to remove catalyst fines and water, and optionally higher boiling point oxygenates and hydrocarbons. The effluent stream is then withdrawn from the quench device to an optional compression step. In one embodiment, the compressor is a single compression stage or comprises more than one compression stages. After compression, the effluent stream is further processed by washing to remove carbon dioxide and other oxygenates and drying to remove water as described below.

Oxygenates are optionally removed from the effluent stream by extraction with an oxygenate wash medium. An oxygenate wash medium is any medium that preferentially adsorbs oxygenates over olefin(s). The oxygenate wash tower has an inlet stream comprising the oxygenate wash medium. The effluent stream enters the wash tower through an inlet in the bottom of the oxygenate wash tower. The effluent stream travels upward through the oxygenate wash tower. The oxygenate wash medium travels downward counter current from the flow of the effluent stream. This counter current flow causes the oxygenate wash medium to contact the effluent steam and extract the oxygenates in the oxygenate wash tower into the oxygenate wash medium. The absorbed oxygenates and oxygenate wash medium are removed from the bottom of the oxygenate wash tower.

All or a portion of the oxygenates such as ethers, aldehydes and/or ketones that are remaining in the quenched effluent stream are optionally removed during the oxygenate wash step. In one preferred embodiment, all or a portion of oxygenates such as dimethyl ether, acetaldehyde, acetone, propanal and/or propanone are optionally removed in the oxygenate wash tower.

Examples of oxygenate wash mediums include alcohols, amines, amides, nitrites, heterocyclic nitrogen containing compounds, or a combination of any of the preceding. Either monohydric alcohols or polyhydric alcohols can be used as the alcohol absorbent. Specific examples of absorbents include methanol, ethanol, propanol, ethylene glycol, diethylene glycol, triethylene glycol, ethanolamine, diethanolamine, triethanolamine, hindered cyclic amines, acetonitrile, n-methylpyrrolidone, dimethyl formamide, and combinations thereof.

In one embodiment, a distillation tower fractionates the quenched effluent stream at a location downstream from the quench tower and upstream from the apparatus for drying the effluent stream. The purpose of the distillation tower is to separate ethylene and propylene from one or more byproduct selected from a group consisting of methanol, dimethyl ether, propane, acetaldehyde, and C4+ hydrocarbons. The distillation tower is sometimes referred to as an oxygenate rejection tower due to its ability to remove the aforementioned oxygenates from a fraction comprising the desired ethylene and propylene. The ethylene and propylene are components of the overhead fraction. Methanol, dimethyl ether, acetaldehyde, and other C4+ hydrocarbons are components of the bottoms fraction. The bottoms fraction of the oxygenate rejection tower optionally requires isolation of one or more byproduct streams, typically a butylene stream, a C5+ stream, a propane stream for various uses. It is desirable to use one or more embodiments of the present invention to separate methanol, ethanol and/or dimethyl ether from a C3+ hydrocarbon stream (typically a propane stream or a butylene stream).

Next, in one embodiment, the effluent stream passes through an alkaline wash tower. An alkaline wash tower is a step where the effluent stream is contacted with an alkaline wash medium. The alkaline wash tower removes carbon dioxide from the quenched effluent stream by contacting quenched effluent stream with an alkaline wash medium according to one embodiment.

The alkaline wash medium is an aqueous medium that has a pH greater than 7. Examples of such alkaline wash mediums include amines, potassium carbonate, and caustic. The term "caustic" as used herein refers to group 1 metal hydroxides such as potassium hydroxide and sodium hydroxide. The alkaline wash tower of one embodiment has an alkaline wash stage and a water wash stage. In an embodiment, the alkaline wash stage washes the quenched effluent stream with an alkaline stream having a pH greater than about 13. According to one embodiment, the alkaline stream, containing one or more alkaline compositions, has an alkaline concentration of 1 wt. % or more, preferably from about 1 wt. % to about 15 wt. %, more preferably from about 2 wt. % to about 5 wt. %, most preferably of about 3 wt. % based upon the total weight of the alkaline stream. In another embodiment the concentration of alkaline in the alkaline stream is from about 5 wt. % to about 20 wt. % preferably from about 5 wt. % to about 15 wt. % most preferably about 10 wt. % based upon the total weight of the alkaline stream.

The quenched effluent stream passes through an additional stage of washing referred to as the water wash stage where the effluent stream is contacted in a countercurrent flow with water. The water washing stage removes any remaining caustic in the effluent stream.

A drying step is optionally included to follow the water washing stage. In this embodiment, a solid or liquid drying system can be used to remove water and/or additional oxygenate from the effluent stream.

In the solid drying system, the effluent stream having been quenched and optionally alkaline washed and water washed is contacted with a solid adsorbent to further remove water and oxygenates to very low levels. Typically, the adsorption process is carried out in one or more fixed beds containing a suitable solid adsorbent.

Adsorption is useful for removing water and oxygenates to very low concentrations, and for removing oxygenates that may not normally be removed by using other treatment systems. Preferably, an adsorbent system used as part of this invention has multiple adsorbent beds. Multiple beds allow for continuous separation without the need for shutting down the process to regenerate the solid adsorbent. By way of example and not by limitation, a three bed system typically has one bed that is on-line, one bed regenerated off-line, and a third bed on stand-by.

The specific adsorbent solid or solids used in the adsorbent beds depends on the types of contaminants being removed. Non-limiting examples of solid adsorbents for removing water and various polar organic compounds, such as oxygenates and absorbent liquids, include aluminas, silica, 3A molecular sieves, 4A molecular sieves, and alumino-silicates. Beds containing mixtures of these sieves or multiple beds having different adsorbent solids are used to remove water, as well as a variety of oxygenates in one embodiment.

In an embodiment of the present invention, one or more adsorption beds are arranged in series or parallel. In one example of a series arrangement, a first bed is used to remove the smallest and most polar molecules, which are the easiest to remove. Subsequent beds for removing larger less polar oxygenated species are next in series. As a specific example of one type of arrangement, water is first selectively removed using a 3A molecular sieve. This bed is then followed by one or more beds containing one or more less selective adsorbents such as a larger pore molecular sieve e.g. 13x and/or a high surface area active alumina.

In another embodiment, the first bed is a 3.6 A molecular sieve capable of selectively separating both water and methanol from the hydrocarbons in the olefin stream. This first bed can then be followed by one or more 13X or active alumina beds as described above.

The adsorbent beds can be operated at ambient temperature or at elevated temperature as required, and with either upward or downward flow. Regeneration of the adsorbent materials can be carried out by conventional methods including treatment with a stream of a dry inert gas such as nitrogen at elevated temperature.

In the liquid drying system, a water absorbent is used to remove water from the effluent stream. The water absorbent can be any liquid effective in separating water from an olefin stream. Preferably, the water absorbent is a polyol or an alcohol, such as ethanol or methanol.

The step of drying produces a dried effluent stream that is hereinafter referred to as the olefin product stream.

The effluent stream following the step of drying is referred to as the dried olefin stream, or olefin product stream. The dried olefin stream or olefin product stream is further processed to isolate and purify components in the olefin product stream, particularly, ethylene and propylene into ethylene and propylene streams, respectively. There are many well-known recovery systems, techniques and sequences that are useful in separating olefin(s) and purifying olefin(s) in the olefin product stream. Recovery systems generally comprise one or more or a combination of a various separation, fractionation and/or distillation towers, columns, splitters, or trains, reaction systems and other associated equipment, for example, various condensers, heat exchangers, refrigeration systems or chill trains, compressors, knock-out drums or pots, pumps, and the like.

Non-limiting examples of equipment used in a recovery system include one or more of a demethanizer, preferably a high temperature demethanizer, a dethanizer, a depropanizer, membranes, ethylene (C2) splitter, propylene (C3) splitter, butylene (C4) splitter, and the like.

According to one embodiment, the method of the present invention for separating or removing methanol, ethanol and/or dimethyl ether from a C3+ hydrocarbon stream is useful on one or more product or byproducts streams in the recovery section. Particularly, it is helpful to separate or remove methanol, ethanol and/or dimethyl ether from a propane stream or a C4+ stream. Particularly, the one or more techniques disclosed in here for separation of dimethyl ether from a C3+ hydrocarbon stream is useful on the bottoms stream of a C3 splitter or the overhead or bottoms stream of a debutanizer. The method of separating or removing dimethyl ether from a C3+ hydrocarbon stream according to one or more embodiments of the present invention is suitable for a guard bed function.

Various recovery systems useful for recovering predominately olefin(s), preferably prime or light olefin(s) such as ethylene, propylene and/or butylene are described in U.S. Pat. No. 5,960,643 (secondary rich ethylene stream), U.S. Pat. Nos. 5,019,143, 5,452,581 and 5,082,481 (membrane separations), U.S. Pat. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefin(s) without superfractionation), and U.S. Pat. No. 6,293,998 (pressure swing adsorption), which are all herein fully incorporated by reference.

Generally accompanying most recovery systems is the production, generation or accumulation of additional products, by-products and/or contaminants along with the preferred prime products. The preferred prime products, the light olefin(s), such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in an oxygenate-to-olefin process are passed through a purification system that removes low levels of by-products or contaminants.

Non-limiting examples of contaminants and by-products include generally polar compounds such as water, alcohols, carboxylic acids, ethers, carbon oxides, ammonia and other nitrogen compounds, arsine, phosphine and chlorides. Other contaminants or by-products include hydrogen and hydrocarbons such as acetylene, methyl acetylene, propadiene, butadiene and butyne.

Other recovery systems that include purification systems, for example, for the purification of olefin(s), are described in Kirk-Othmer Encyclopedia of Chemical Technology, 4th Edition, Volume 9, John Wiley & Sons, 1996, pages 249–271 and 894–899, which is herein incorporated by reference. Purification systems are also described in, for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000 (purge stream using hydrating catalyst), which is herein incorporated by reference.

Typically, in converting one or more oxygenates to olefin(s) having 2 or 3 carbon atoms, an amount of hydrocarbons, particularly olefin(s), especially olefin(s) having 4 or more carbon atoms, and other by-products are formed or produced. Included in the recovery systems of the invention are reaction systems for converting the products contained within the olefin product stream withdrawn from the reactor or converting those products produced as a result of the recovery system utilized.

In one embodiment, the olefin product stream is passed through a recovery system producing one or more hydrocarbon containing stream(s), in particular, a three or more carbon atom (C3+) hydrocarbon containing stream. In this embodiment, the C3+ hydrocarbon containing stream is passed through a first fractionation zone producing a crude C3 hydrocarbon and a C4+ hydrocarbon containing stream, the C4+ hydrocarbon containing stream is passed through a second fractionation zone producing a crude C4 hydrocarbon and a C5+ hydrocarbon containing stream. The four or more carbon hydrocarbons include butylenes such as butylene-1 and butylene-2, butadienes, saturated butanes, and isobutanes.

The olefin product stream removed from a conversion process, particularly an oxygenate-to-olefin process, typically contains hydrocarbons having 4 or more carbon atoms. The amount of hydrocarbons having 4 or more carbon atoms is typically in an amount less than 30 weight percent, preferably less than 25 weight percent, more preferably less than 20 weight percent, and most preferably less than 15 weight percent, based on the total weight of the olefin product stream withdrawn from an oxygenate-to-olefin process, excluding water. In particular with a conversion process of oxygenates into olefin(s) utilizing a molecular sieve catalyst composition the resulting olefin product stream typically comprises a majority of ethylene and/or propylene and a lesser amount of four carbon and higher carbon number products and other by-products, excluding water.

The preferred light olefin(s) produced by any one of the processes described above, preferably conversion processes, are high purity prime olefin(s) products that contains a CX olefin, wherein x is a number from 2 to 4, in an amount greater than 80 wt. %, preferably greater than 90 wt. %, more preferably greater than 95 wt. %, and most preferably no less than about 99 wt. %, based on the total weight of the olefin. The purity of the olefin(s) is preferably of a grade that makes the use of the olefin(s) acceptable for one or more applications discussed below.

Suitable well-known reaction systems that follow the recovery system primarily take lower value products and convert them to higher value products. For example, the C4 hydrocarbons, butylene-1 and butylene-2 are used to make alcohols having 8 to 13 carbon atoms, and other specialty chemicals, isobutylene is used to make a gasoline additive, methyl-t-butylether, butadiene in a selective hydrogenation unit is converted into butylene-1 and butylene-2, and butane is useful as a fuel.

Non-limiting examples of reaction systems that take lower value products and convert them to higher value products include U.S. Pat. No. 5,955,640 (converting a four carbon product into butylene-1), U.S. Pat. No. 4,774,375

(isobutane and butylene-2 alkylated to an alkylate gasoline), U.S. Pat. No. 6,049,017 (dimerization of n-butylene), U.S. Pat. Nos. 4,287,369 and 5,763,678 (carbonylation or hydroformulation of higher olefin(s) with carbon dioxide and hydrogen making carbonyl compounds), U.S. Pat. No. 4,542,252 (multistage adiabatic process), U.S. Pat. No. 5,634,354 (olefin-hydrogen recovery), and Cosyns, J. et al., Process for Upgrading C3, C4 and C5 Olefinic Streams, Pet. & Coal, Vol. 37, No. 4 (1995) (dimerizing or oligomerizing propylene, butylene and pentylene), which are all herein fully incorporated by reference.

Other uses for one or more olefin product(s) are disclosed in U.S. Pat. No. 6,121,503 (making plastic with an olefin product having a paraffin to olefin weight ratio less than or equal to 0.05), U.S. Pat. No. 6,187,983 (electromagnetic energy to reaction system), PCT WO 99/18055 publishes Apr. 15, 1999 (heavy hydrocarbon in the olefin product stream fed to another reactor) PCT WO 01/60770 published Aug. 23, 2001 and U.S. patent application Ser. No. 09/627,634 filed Jul. 28, 2000 (high pressure), U.S. patent application Ser. No. 09/507,838 filed Feb. 22, 2000 (staged feedstock injection), and U.S. patent application Ser. No. 09/785,409 filed Feb. 16, 2001 (acetone co-fed), which are all herein fully incorporated by reference.

In another embodiment, olefin(s) produced are directed to, in one embodiment, one or more polymerization processes for producing various polyolefin(s). (See for example, U.S. patent application Ser. No. 09/615,376 filed Jul. 13, 2000 that is herein fully incorporated by reference.)

Polymerization processes include solution, gas phase, slurry phase and a high-pressure process, or a combination thereof. Particularly preferred is a gas phase or a slurry phase polymerization of one or more olefin(s) at least one of which is ethylene or propylene. Polymerization processes include those non-limiting examples described in the following: U.S. Pat. Nos. 4,543,399, 4,588,790, 5,028,670, 5,317,036, 5,352,749, 5,405,922, 5,436,304, 5,453,471, 5,462,999, 5,616,661, 5,627,242, 5,665,818, 5,677,375, 5,668,228, 5,712,352 and 5,763,543 and EP-A-0 794 200, EP-A-0 802 202, EP-A2-0 891 990 and EP-B-0 634 421 describe gas phase polymerization processes; U.S. Pat. Nos. 3,248,179 and 4,613,484, 6,204,344, 6,239,235 and 6,281,300 describe slurry phase polymerization processes; U.S. Pat. Nos. 4,271,060, 5,001,205, 5,236,998 and 5,589,555 describe solution phase polymerization processes; and U.S. Pat. Nos. 3,917,577, 4,175,169, 4,935,397, and 6,127,497 describe high pressure polymerization processes; all of which are herein fully incorporated by reference.

These polymerization processes utilize a polymerization catalyst that can include any one or a combination of the molecular sieve catalysts discussed above, however, the preferred polymerization catalysts are those Ziegler-Natta, Phillips-type, metallocene, metallocene-type and advanced polymerization catalysts, and mixtures thereof. Non-limiting examples of polymerization catalysts are described in U.S. Pat. Nos. 3,258,455, 3,305,538, 3,364,190, 3,645,992, 4,076,698, 4,115,639, 4,077,904 4,482,687, 4,564,605, 4,659,685, 4,721,763, 4,879,359, 4,960,741, 4,302,565, 4,302,566, 4,302,565, 4,302,566, 4,124,532, 4,302,565, 5,763,723, 4,871,705, 5,120,867, 5,324,800, 5,347,025, 5,384,299, 5,391,790, 5,408,017, 5,491,207, 5,455,366, 5,534,473, 5,539,124, 5,554,775, 5,621,126, 5,684,098, 5,693,730, 5,698,634, 5,710,297, 5,714,427, 5,728,641, 5,728,839, 5,753,577, 5,767,209, 5,770,753 and 5,770,664, 5,527,752, 5,747,406, 5,851,945 and 5,852,146, all of which are herein fully incorporated by reference.

In preferred embodiment, the present invention comprises a polymerizing process of one or more olefin(s) in the presence of a polymerization catalyst system in a polymerization reactor to produce one or more polymer products, wherein the one or more olefin(s) having been made by converting an alcohol, particularly methanol, using a zeolite or zeolite-type molecular sieve catalyst composition. The preferred polymerization process is a gas phase polymerization process and at least one of the olefin(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

Polymerization conditions vary depending on the polymerization process, polymerization catalyst system and the polyolefin produced. Typical conditions of polymerization pressure vary from about 100 psig (690 kpag) to greater than about 1000 psig (3448 kpag), preferably in the range of from about 200 psig (1379 kPag) to about 500 psig (3448kPag), and more preferably in the range of from about 250 psig (1724 kPag) to about 350 psig (2414 kpag). Typical conditions of polymerization temperature vary from about 273K to about 773K, preferably from about 303K to about 623K, more preferably in the range of from about 333K to 523K, and most preferably in the range of from about 343K to about 423K. In the preferred polymerization process the amount of polymer being produced per hour is greater than 25,000 lbs/hr (11,300 Kg/hr), preferably greater than 35,000 lbs/hr (15,900 Kg/hr), more preferably greater than 50,000 lbs/hr (22,700 Kg/hr) and most preferably greater than 75,000 lbs/hr (29,000 Kg/hr).

The polymers produced by the polymerization processes described above include linear low density polyethylene, elastomers, plastomers, high density polyethylene, low density polyethylene, polypropylene and polypropylene copolymers. The propylene-based polymers produced by the polymerization processes include atactic polypropylene, isotactic polypropylene, syndiotactic polypropylene, and propylene random, block or impact copolymers.

Typical ethylene based polymers have a density in the range of from 0.86 g/cc to 0.97 g/cc, a weight average molecular weight to number average molecular weight (Mw/Mn) of greater than 1.5 to about 10 as measured by gel permeation chromatography, a melt index (I2) as measured by ASTM-D-1238-E in the range from 0.01 dg/min to 1000 dg/min, a melt index ratio (I21/I2) (I21 is measured by ASTM-D-1238-F) of from 10 to less than 25, alternatively a I21/I2 of from greater than 25, more preferably greater than 40.

Polymers produced by the polymerization process are useful in such forming operations as film, sheet, and fiber extrusion and co-extrusion as well as blow molding, injection molding and rotary molding; films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications; fibers include melt spinning, solution spinning and melt blown fiber operations for use in woven or non-woven form to make filters, diaper fabrics, medical garments, geotextiles, etc; extruded articles include medical tubing, wire and cable coatings, geomembranes, and pond liners; and molded articles include single and multi-layered constructions in the form of bottles, vessels, large hollow articles, rigid food containers and toys, etc.

In addition to polyolefin(s), numerous other olefin derived products are formed from the olefin(s) recovered any one of the processes described above, particularly the conversion processes, more particularly the GTO process or MTO process. These include, but are not limited to, aldehydes, alcohols, acetic acid, linear alpha olefin(s), vinyl acetate, ethylene dicholoride and vinyl chloride, ethylbenzene, ethylene oxide, cumene, isopropyl alcohol, acrolein, allyl chloride, propylene oxide, acrylic acid, ethylene-propylene rubbers, and acrylonitrile The invention will now be more particularly described with reference to the following Examples and the accompanying drawings.

EXAMPLE 1

Figure 2:
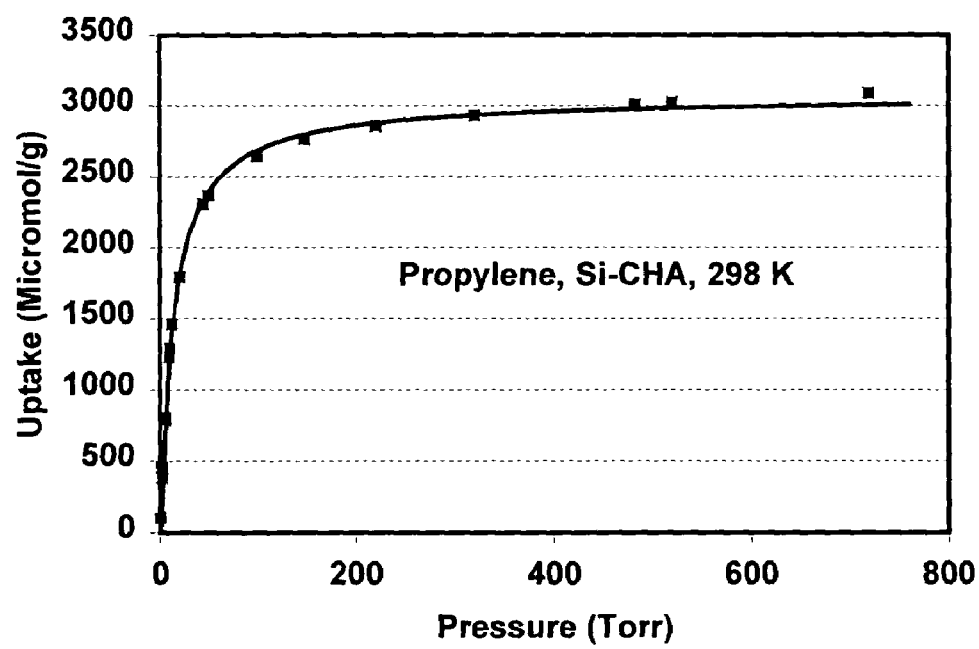
FIG. 2 is a plot showing the adsorption uptake of propylene on Si-CHA at 298K.

FIGS. 1 and 2 show adsorption equilibrium isotherms for dimethyl ether and propylene on silica chabazite (Si-CHA) at 298K, respectively. These figures show that, at 760 Torr, the uptakes are about 13.7wt % (~2980 $\mu$mol/g) for dimethyl ether and about 13wt % (~3095 $\mu$mol/g) for propylene. These are ideally large uptakes that support the utilization of Si-CHA in adsorption-based separation schemes. The adsorption characteristics of methanol and trans-2-butylene on Si-CHA are very similar to those of dimethyl ether and propylene shown in FIGS. 1 and 2 and the uptakes remain high even at relatively high temperatures. The above example shows that the adsorption of dimethyl ether and propylene, as well as methanol and trans-2-butylene, into Si-CHA is sufficient to make Si-CHA an acceptable crystalline microporous material for adsorption of one or more of these components.

EXAMPLE 2

A dynamic technique, frequency response, was employed to measure the diffusion time constants of methanol, dimethyl ether, propane, propylene, and trans-2-butylene on Si-CHA. FIGS. 3–10 summarize typical experiments for these components on Si-CHA at a constant pressure of 2.66 kPa (20 Torr) and various temperatures. In these figures, the frequency (i.e., abscissa) value at which the data goes through a maximum directly gives the diffusion time constant (sec-1) for the corresponding system and conditions (see for example: Reyes et al. in "Frequency Modulation Methods for Diffusion and Adsorption Measurements in Porous Solids", J. Phys. Chem. B. 101, pages 614–622, 1997).

Figure 3:
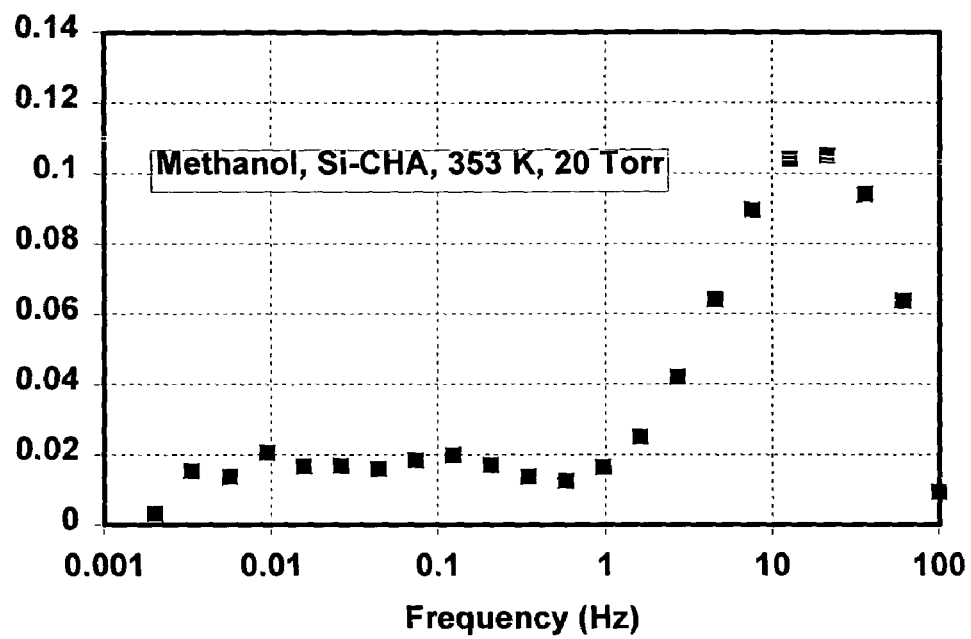
FIG. 3 is a plot showing the frequency response behavior of methanol on Si-CHA at 353K and 20 Torr.
Figure 4:
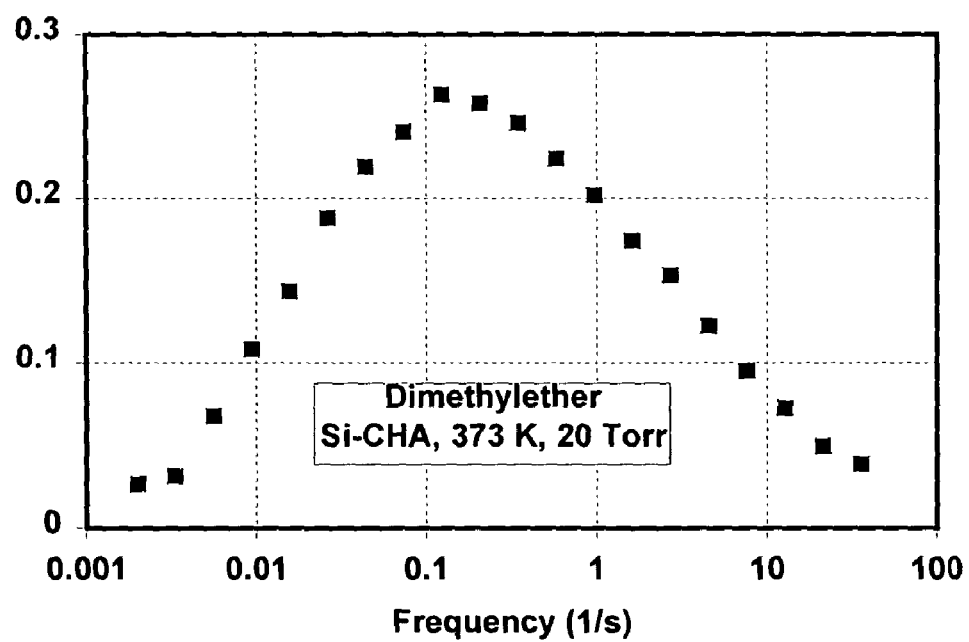
FIG. 4 is a plot showing the frequency response behavior of dimethyl ether on Si-CHA at 373K and 20 torr.
Figure 5:
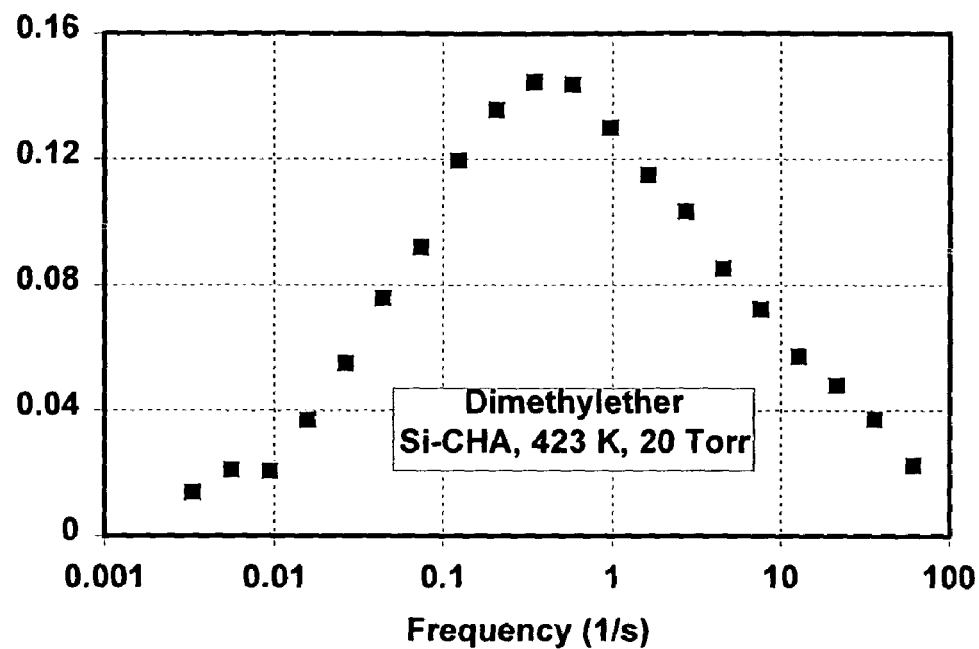
FIG. 5 is a plot showing the frequency response behavior of dimethyl ether on Si-CHA at 423K and 20 torr.
Figure 6:
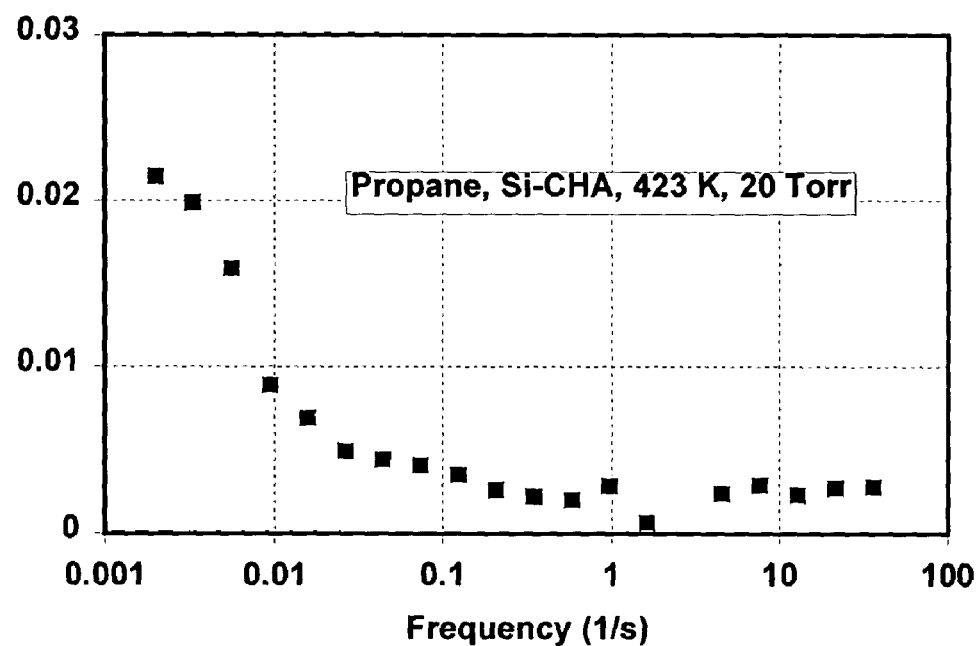
FIG. 6 is a plot showing the frequency response behavior of propane on Si-CHA at 423K and 20 torr.
Figure 7:
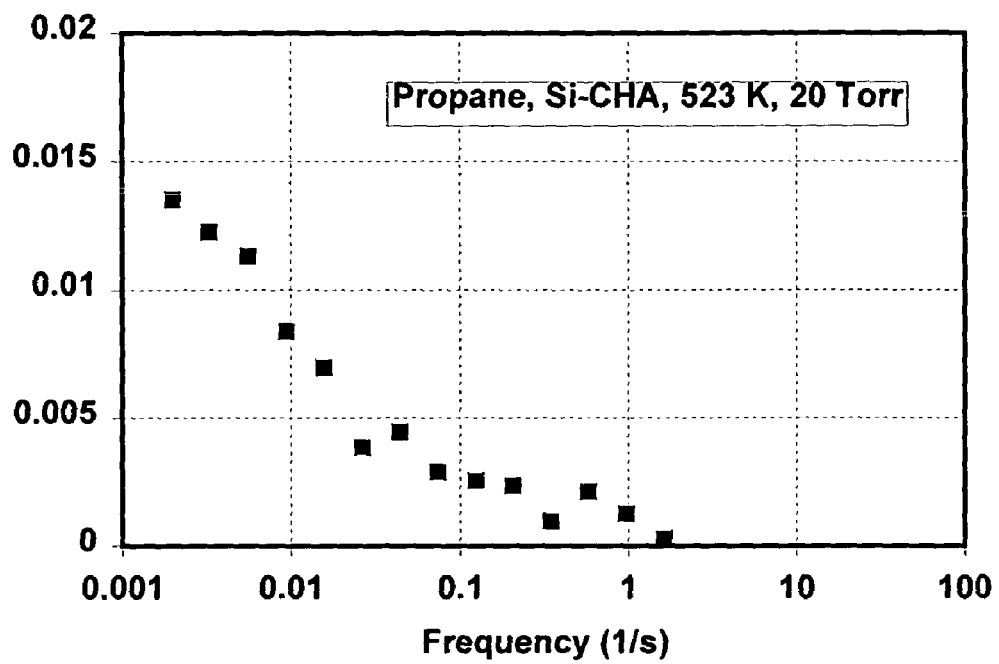
FIG. 7 is a plot showing the frequency response behavior of propane on Si-CHA at 523K and 20 torr.

FIG. 3 shows that the diffusion time constant for methanol at 353K is very large (>10 sec-1). This signal a rapid diffusion process in which methanol is able to reach the interior of the crystals in a fraction of a second. Similarly, FIGS. 4 and 5 show that the diffusion time constants for dimethyl ether at 373K and 423K exceed 0.1 sec-1. Though not as fast as methanol, dimethyl ether is able to diffuse into the material within a few seconds. This is in high contrast to molecules like propane (and other higher hydrocarbons and oxygenates) that take much longer to diffuse into the crystals. For example, FIG. 6 and 7 show that the diffusion time constant for propane is about 2 orders of magnitude smaller than for dimethyl ether at the same conditions of pressure and temperature. For propane, the frequency at which the data goes through a maximum is below the lower frequency limit of the experiments (0.001 sec-1). This very low rate of diffusion for propane strongly suggests that by suitably controlling the cycle time in a pressure swing operation, methanol and dimethyl ether can be selectively adsorbed from the mixture while rejecting propane and other higher hydrocarbons and oxygenates.

Figure 8:
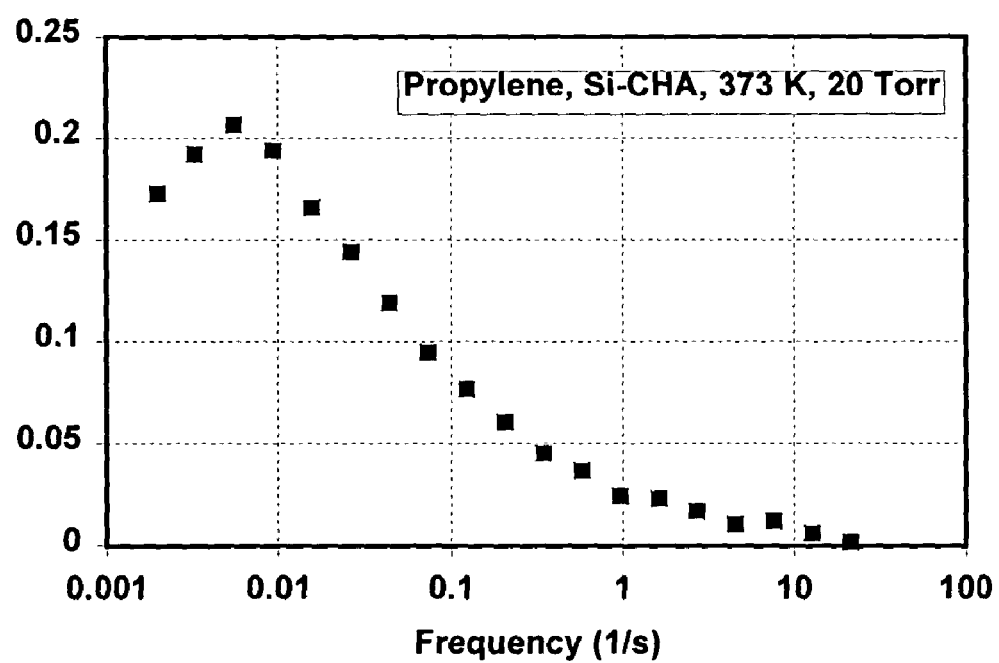
FIG. 8 is a plot showing the frequency response behavior of propylene on Si-CHA at 373K and 20 torr.
Figure 9:
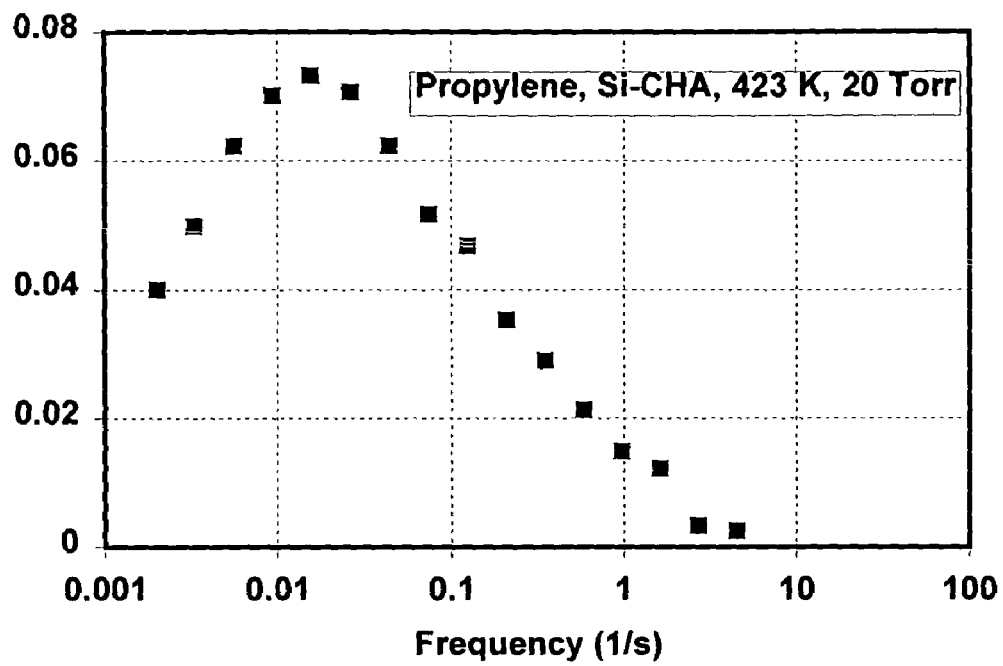
FIG. 9 is a plot showing the frequency response behavior of propylene on Si-CHA at 423K and 20 torr.
Figure 10:
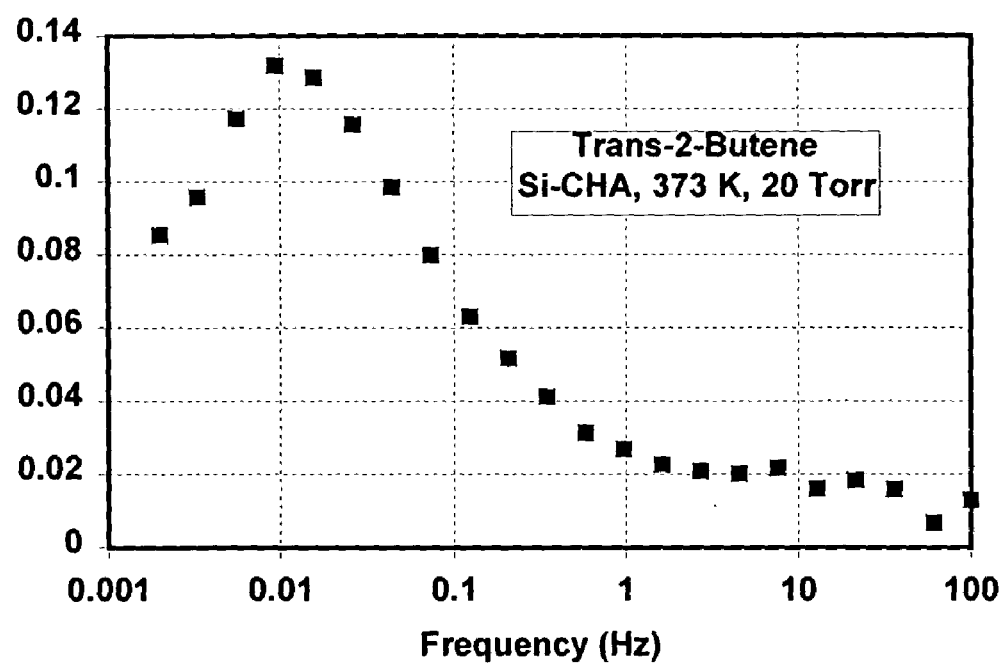
FIG. 10 is a plot showing the frequency response behavior of tans-2-butene on Si-CHA at 373K and 20 Torr.

FIGS. 8–10 show that Si-CHA can also adsorb propylene and trans-2-butylene. These figures show that the diffusion time constants for propylene and trans-2-butylene are of the order of 0.01 sec-1. Thus, if the duration of the adsorption cycle is designed for about 2 minutes, Si-CHA can also selectively adsorb propylene and trans-2-butylene, in addition to methanol and dimethyl ether, while rejecting propane and other hydrocarbons and oxygenates. If the duration of the adsorption cycle is appropriately selected, Si-CHA can preferentially adsorb methanol and dimethyl ether over propylene and trans-2-butylene.

The foregoing description of the invention including but not limited to drawings and examples are intended to illustrate one or more embodiments of the invention and are non-limiting. While the invention has been illustrated an described herein in terms of the advantages, features, and applications disclosed, it will be apparent to a person of ordinary skill in the art that the invention can be used in other instances. Other modifications and improvements can be made without departing from the scope of the invention as defined by the following claims.

What is claimed is:

1. A process for making a propylene stream and a propane stream from an oxygenate feed stream comprising the steps of:
   (a) contacting an oxygenate feed stream with a molecular sieve catalyst under conditions sufficient to make a first stream, the first stream comprises, propylene, propane and dimethyl ether;
   (b) separating at least a majority of propane in the first stream from propylene in the first stream to farm a propylene product stream; and
   (c) adsorbing dimethyl ether from propane with a crystalline microporous material that preferentially adsorbs dimethyl ether over propane to form a propane stream.

2. The process of claim 1, further comprising the step of desorbing the dimethyl ether from the adsorbent bed.

3. The process of claim 2, wherein the steps of adsorbing and desorbing are in a kinetic-based pressure andlor temperature swing adsorption process.

4. The process of claim 3, wherein the crystalline microporous material preferentially adsorbs dirnethyl ether within an adsorption time of about 120 seconds or less.

5. The process of claim 4, wherein the adsorption time is about 90 seconds or less.

6. The process of claim 4, wherein the adsorption time is about 60 seconds or less.

7. The process of claim 1, wherein the step of (c) adsorbing occurs within a temperature ranging from about 273K to about 523K.

8. The process of claim 1, wherein the step (c) of adsorbing occurs within a pressure ranging from about 100 kPa to about 2000 kPa.

9. The process of claim 1, wherein the first stream is in a vapor phase during the step (c) of adsorbing.

10. The process of claim 1, wherein the first stream further comprises C4+ hydrocarbons.

11. The process of claim 1, wherein the crystalline microporous material has a system of three interconnecting 8-membered ring channels.

12. The process of claim 1, wherein the first stream comprises methanol during the step (b) of separating.

13. The process of claim 12, wherein the first stream comprises water during the step (b) of separating.

* * * * *